US008158782B2

(12) United States Patent
Hovinen

(10) Patent No.: US 8,158,782 B2
(45) Date of Patent: Apr. 17, 2012

(54) BIOMOLECULE LABELING REACTANTS BASED ON AZACYCLOALKANES AND CONJUGATES DERIVED THEREOF

(75) Inventor: Jari Hovinen, Raisio (FI)

(73) Assignee: Wallac Oy, Turku (FI)

( * ) Notice: Subject to any disclaimer, the term of this patent is extended or adjusted under 35 U.S.C. 154(b) by 681 days.

(21) Appl. No.: 12/298,143

(22) PCT Filed: May 4, 2007

(86) PCT No.: PCT/FI2007/050248
§ 371 (c)(1),
(2), (4) Date: Oct. 23, 2008

(87) PCT Pub. No.: WO2007/128874
PCT Pub. Date: Nov. 15, 2007

(65) Prior Publication Data
US 2009/0156801 A1 Jun. 18, 2009

Related U.S. Application Data

(60) Provisional application No. 60/797,658, filed on May 5, 2006.

(30) Foreign Application Priority Data

May 8, 2006 (FI) .................................... 20065299

(51) Int. Cl.
*C07D 255/02* (2006.01)
*C07D 257/02* (2006.01)
(52) U.S. Cl. ..................................... 540/474
(58) Field of Classification Search .......... None
See application file for complete search history.

(56) References Cited

U.S. PATENT DOCUMENTS

| | | | |
|---|---|---|---|
| 5,053,503 | A | 10/1991 | Dean et al. |
| 5,334,711 | A | 8/1994 | Sproat et al. |
| 5,612,215 | A | 3/1997 | Draper et al. |
| 5,672,695 | A | 9/1997 | Eckstein et al. |
| 6,949,639 | B1 | 9/2005 | Hovinen et al. |
| 6,949,696 | B2 | 9/2005 | Fincher et al. |
| 2003/0118999 | A1 | 6/2003 | Hovinen |
| 2005/0084451 | A1 | 4/2005 | Hovinen et al. |

FOREIGN PATENT DOCUMENTS

| | | |
|---|---|---|
| WO | WO 87/05030 | 8/1987 |
| WO | WO 89/01475 A1 | 2/1989 |
| WO | WO 92/07065 A1 | 4/1992 |
| WO | WO 2005/058877 A1 | 6/2005 |

OTHER PUBLICATIONS

Supplementary European Search Report issued in the corresponding European Application No. 07730735.3-2101 dated Jul. 5, 2010.
Form PCT/ISA/210 (International Search Report) dated Aug. 31, 2007.
Form PCT/ISA/237 (Written Opinion of the International Searching Authority) dated Jul. 13, 2007.
Finnish Search Report (with English language translation of category of cited documents) dated Mar. 13, 2007.
Aime, Silvio et al., "Lanthanide(III) Chelates for NMR Biomedical Applications", Chemical Society Reviews, 1998, vol. 27, pp. 19-29.
Brossette, Thierry et al., "Synthesis of Polyphosphorylated AZT Derivatives for the Development of Specific Enzyme Immunoassays", J. Org. Chem, 1999, vol. 64, No. 14, pp. 5083-5090, American Chemical Society.
Brucher, E., et al, "Synthesis, Equilibrium, and Kinetic Properties of the Gadolinium(III) Complexes of Three Triazacyclodecanetriacetate Ligands", Inorg. Chem, 1991, vol. 30, No. 9, pp. 2092-2097, American Chemical Society.
Caravan, Peter et al., "Gadolinium(III) Chelates as MRI Contrast Agents: Structure, Dynamics, and Applications", Chem. Rev., 1999, vol. 99, No. 9, pp. 2293-2352, American Chemical Society.
De Leon-Rodriguez, Luis M. et al., "Solid-Phase Synthesis of DOTA-Peptides", Chem. Eur. J., 2004, vol. 10, pp. 1149-1155, Wiley-VCH Verlag GmbH & Co. KGaA, Weinheim.
Fichna, Jakub et al., "Synthesis of Target-Specific Radiolabeled Peptides for Diagnostic Imaging", Bioconjugate Chem., 2003, vol. 14, No. 1, pp. 3-17, American Chemical Society.
Heppeler, A, et al., "Radiometal-Labelled Macrocyclic Chelator-Derivatised Somatostatin Analogue With Superb Tumour-Targeting Properties and Potential for Receptor-Mediated Internal Radiotherapy", Chem. Eur. J., 1999, vol. 5, No, 7, pp. 1974-1981, Wiley-VCH Verlag GmbH, Weinhiem.
Hovinen, Jari et al., "Novel Non-Nucleosidic Phosphoramidite Building Blocks for Versatile Functionalization of Oligonucleotides at Primary Hydroxy Groups", J. Chem. Soc. Perkin Trans., 1994, pp. 2745-2749.
Hovinen, Jari et al., "Novel Solid Supports for the Preparation of 3'-Derivatized Oligonucleotides: Introduction of 3'-Alkylphosphate Tether Gropups Bearing Amino, Carboxy, Carboxamido, and Mercapto Functionalities", Tetrahedron, 1994. vol. 50, No, 24, pp. 7203-7218, Pergamon.
Hovinen, Jari et al., "Imidazole Tethered Oligodeoxyribonucleotides: Synthesis and RNA Cleaving Activity", J. Org. Chem., 1995, vol. 60, No, 7, pp. 2205-2209, American Chemical Society.
Hovinen, Jari et al., "C-Glycoside Phosphoramidite Building Block for Versatile Functionalization of Oligodeoxyribonucleotides", J, Chem. Soc. Perkins Trans., 1997, vol. 1, pp. 3017-3020.
Hovinen, Jari, "Synthesis of Carbon-3-Substituted 1,5,9-Triazacyclododecanes, RNA Cleavage Agents Suitable for Oligonucleotide Tethering", Bioconjugate Chem., 1998, vol. 9, No. 1, pp. 132-136, American Chemical Society.
Hovinen, Jari et al., "Versatile Strategy for Oligonucleotide Derivatization. Introduction of Lanthanide(III) Chelates to Oligonucleotides", Organic Letters, 2001, vol. 3, No. 16, pp. 2473-2476, American Chemical Society.
Hovinen, Jari et al., "Synthesis of Azamacrocycles Via a Mitsunobu Reaction", Tetrahedron Letters, 2005, vol. 46, pp. 4387-4389, Elsevier.
Jaakkola, Lassi et al., "Versatile Synthesis of MRI Contrast Agents Based on Carbon-Substituted Triazacycloalkanes", Letters in Organic Chemistry, 2006, vol. 3, No. 8, pp. 643-647, Bentham Science Publishers Ltd.

(Continued)

*Primary Examiner* — Noble Jarrell
(74) *Attorney, Agent, or Firm* — Buchanan Ingersoll & Rooney PC

(57) ABSTRACT

This invention concerns novel labeling reactants based on azacycloalkanes, wherein a suitable group is linked to the molecule allowing introduction of the said molecules to bioactive molecules in solution or on solid phase.

8 Claims, 7 Drawing Sheets

OTHER PUBLICATIONS

Kurosawa, Wataru et al., "Preparation of Secondary Amines From Primary Amines Via 2-Nitrobenzenesulfonamides: N-(4-Methoxybenzyl_-3-Phenylpropylamine [Benzenepropanamine, N-[(4-Methoxyphenyl)Methyl]-]", Org, Synth., 2002, vol. 79, pp. 186-195.

Liu, Shuang et al,, "Bifuncitonal Chelators for Therapeutic Lanthanide Radiopharmaceuticals", Bioconjugate Chem., 2001, vol. 12, No. 1, pp. 7-34, American Chemical Society.

Monaco, Vania et al., "Synthesis and Biological Evaluation of Modified DNA Fragments for the Study of Nucleotide Excision Repair in *E. coli*", Nucleosides & Nucleotides, 1999, vol. 18, No. 6 & 7, pp. 1339-1341, Marcel Dekker, Inc.

Niittymäki, Teija et al., "Artificial Ribonucleases", Organic & Biomolecular Chemistry, 2006, vol. 4, pp. 15-25, The Royal Society of Chemistry.

Peuralahti, Jari et al., "Introduction of Lanthanide(III) Chelates to Oligopeptides on Solid Phase", Bioconjugate Chem., 2002, vol. 13, pp. 870-875, American Chemical Society.

Peuralahti, Jari et al., "Labeling of Steroids on Solid Phase", Bioconjugate Chem., 2004, vol. 15, No. 4, pp. 927-930, American Chemical Society.

Peuralahti, Jari et al., "Synthesis of Building Blocks for Solid-Phase Introduction of Diethylenetriaminepentaacetic Acid (DTPA) to Oligonucleotides and Oligopeptides", Bioconjugate Chem., 2006, vol. 17, No. 3, pp. 855-859, American Chemical Society.

Raymond, Kenneth N. et al., "Next Generation, High Relaxivity Gadolinium MRI Agents", Bioconjugate Chem., 2005, vol. 16, No. 1, pp. 3-8, American Chemical Society.

Rogers, Buck E. et al., "Comparison of Four Bifunctional Chelates for Radiolabeling Monoclonal Antibodies With Copper Radioisotopes: Biodistribution and Metabolism", Bioconjugate Chem., 1996, vol. 7, No. 4, pp. 511-522, American Chemical Society.

Rosendale, Brian E. et al., "Biosynthesized [$^{35}$S]Methionine-Labeled Pro-Opiomelanocortin Peptides As Novel Recovery Markers in Radioimmunoassay of Peptide Hormones", Clinical Chemistry, 1985, vol. 31, No. 12, pp. 1965-1968.

Takalo, Harri et al., "Synthesis of Europium(III) Chelates Suitable for Labeling of Bioactive Molecules", Bioconjugate Chem., 1994, vol. 5, No. 3, pp. 278-282, American Chemical Society.

Takalo, Harri et al., "71. Sysnthesis and Luminescence of Novel EU$^{III}$ Complexing Agents and Labels With 4-(Phynylethynyl)Pyridine Subunits", Helvetica Chimica Acta, 1996, vol. 79, pp. 789-802.

Tuchscherer, G., "Template Assembled Synthetic Proteins: Condensation of a Multifunctional Peptide to a Topological Template Via Chemoselective Ligation", 1993, vol. 34, No. 52, pp. 8419-8422, Pergamon Press Ltd.

Volkert, Wynn A. et al., "Therapeutic Radiopharmaceuticals", Chemical Reviews., 1999, vol. 99, No. 9, pp. 2269-2292, American Chemical Society.

Woods, Mark et al., "Targeted Complexes of Lanthanide(III) Ions as Therapeutic and Diagnostic Pharmaceuticals", Journal of Supramolecular Chemistry, 2002, vol. 2, pp. 1-15, Elsevier.

Ziessel, Raymond et al., "Lanthanide Probes for Luminescence Microscopy and Anion Sensing", Journal of Alloys and Compounds, 2004, vol. 374, pp. 283-288, Elsevier.

BIOMOLECULE LABELING REACTANTS BASED ON AZACYCLOALKANES AND CONJUGATES DERIVED THEREOF

FIELD OF THE INVENTION

This invention relates to novel derivatives of azacycloalkanes which allow introduction of the said derivatives to bioactive molecules.

BACKGROUND OF THE INVENTION

The publications and other materials used herein to illuminate the background of the invention, and in particular, cases to provide additional details respecting the practice, are incorporated by reference.

Because of their excellent metal chelating properties derivatives of azamacrocycles are widely used as organic ligands in magnetic resonance imaging (MRI) and positron emission tomography (PET) [Aime, S., Botta, M., Fasano, M. and Terreno, E. 1998, Chem. Soc. Rev., 27, 19, Caravan, P., Ellison, J. J., McMurry, T. J. and Lauffer, R. B., 1999, Chem. Rev., 99, 2293, Woods, M., Kovacs, Z. and Sherry, A. D., 2002, J. Supramol. Chem., 2, 1]. Covalently linked to bioactive molecules certain azamacrocycles have been used as target-specific radiopharmaceuticals [Volkert, W. A. and Hoffman, T. J., 1999, Chem. Rev. 99, 2269, Liu, S., Scott, D. S., 2001, Bioconjugate Chem., 12, 7]. Oligonucleotides tethered to triazacycloalkanes, in turn, have been shown to be site-specific RNA cleavage agents [Niittymäki, T. Lönnberg, H., 2006, Org. Biomol. Chem. 4, 15] which may be used in the future in chemotherapy as chemically reactive antisense oligonucleotides. Lanthanide(III) chelates based on 1,4,7-triazacyclononane are among the brightest stable lanthanide (III) chelates synthesized [Takalo, H., Hemmilä, I., Sutela, T., Latva, M., 1996, helv. Chim. Acta, 79, 789, Ziessel, R., Charbonniere, L. J., 2004, J. Alloys Comp. 374, 283]. These types of labels may be extremely useful in in vitro diagnostics based on time-resolved fluorescence technology.

In several applications, covalent conjugation of azamacrocycles to bioactive molecules is required. Most commonly, this is performed in solution by allowing an amino or mercapto group of a bioactive molecule to react with isothiocyanato, maleimido or N-hydroxysuccinimido derivatives of the azamacrocycle [Fichna, J., Janecka, A., 2003, Bioconjugate Chem., 14, 3]. Since in all the cases the reaction is performed with an excess of an activated label, laborious purification procedures cannot be avoided. Especially, when attachment of several label molecules, or site-specific labeling in the presence of several functional groups of similar reactivities is required, the isolation and characterization of the desired biomolecule conjugate is extremely difficult, and often practically impossible.

For oligonucleotide derivatization, an alternative tethering strategy has been developed. It involves solid phase synthesis of oligonucleotides containing an electrophilic ester [Hovinen, J., Guzaev, A., Azhayev, A., Lönnberg, H., 1994, Tetrahedron, 50, 7203, Hovinen, J., Guzaev, A., Azhayev, A., Lönnberg, H., 1994, J. Chem. Soc. Perkin Trans 1, 2745] or thioester linker [Hovinen, J., Guzaev, A., Azhayeva, E., Azhayev, A., Lönnberg, H., 1995, J. Org. Chem. 60, 2205, Hovinen, J. Salo, H., 1997, J. Chem. Soc. Perkin Trans 1, 3017], and cleavage of the linker with appropriate azamacrocycles tethered to an amino group [Hovinen, J. 1998, Bioconjugate Chem. 9, 132] giving rise to oligonucleotide conjugates where the azamacrocycle is incorporated to the oligonucleotide structure via an amide bond. Similar tethering strategy has been applied also to oligopeptide derivatization [Tuchscherer, G., 1993, Tetrahedron Lett., 34, 8419]. Although the derivatization proceeds smoothly and the desired biomolecule conjugates can be obtained in high yield, a large excess of the nucleophile, i.e. the azamacrocycle is required. Accordingly, the method is not practical if complicated structures have to be incorporated. In these cases it is highly desirable to couple the label to the biomolecule structure during chain assembly as appropriate building blocks. Accordingly, the purification problems can be avoided by performing the labeling reaction on solid phase. Hence, most of the impurities can be removed by washings when the biomolecule conjugate is still anchored to the solid support, and after release to the solution, only one chromatographic purification is needed. Synthesis of such blocks which allow introduction azamacrocycles to oligopeptides [Heppeler, A., Froilevaux, S., Mäcke, H. R., Jermann, H. E., Béhé, M., Powell, P., and Hennig, M., 1999, Chem. Eur. J., 1, 1974, De Leon-Rodriguez, Kovacs, Z., Dieckmann, G. R., Sherry, A. D., 2004, Chem. Eur. J., 1, 1974, 10, 1149.] and oligonucleotides have been demonstrated.

Solution phase labeling of large biomolecules, such as proteins cannot be avoided. In these cases, the labeling reaction has to be as selective, and purification of the biomolecule conjugate as effective as possible.

Although numerous excellent MRI contrast agents have been synthesized [Raymond, K. N., Pierre, V. C., 2005, Bioconjugate Chem., 16, 3], the macrocyclic chelator, Gd(III) DOTA (1,4,7,10-tetraazacyclododecane-1,4,7,10-tetraacetic acid, Dotarem) is still one of the most commonly used. However, the properties of Gd(III) DOTA are not optimal. The net charge of −1 may cause problems in several applications. The chelate distributes thorough the extracellular and intravascular fluid spaces, but does not cross an intact blood-brain barrier. Naturally, bioactive molecules labeled with this type of chelates have lower cell permeability than the corresponding intact molecules [Rogers, B. E., Anderson, C. J., Connett, J. M., Guo, L. W., Edwards, W. B., Sherman, E. L., Zinn, K. R., Welch, M. J., 1996, Bioconjugate Chem. 7, 511]. Furthermore, the negatively charged chelates may bind unselectively to positively charged binding sites of target molecules, such as antibodies, via electrostatic interactions which may result in low recoveries [Rosendale, B. E., Jarrett, D. B., 1985, Clin. Chem., 31, 1965]. Naturally, all these above mentioned problems will be even more serious when the target molecule is labeled with several charged chelates [Peuralahti, J., Suonpää, K., Blomberg, K., Mukkala, V.-M., Hovinen, J. 2004, Bioconjugate Chem. 15, 927]. To overcome these problems, several neutral chelating agents have been synthesized, among which chelates based on 1,4,7-triazacyclononanetriacetic acid (TETA) are the most common. Although the water proton relaxivity of Gd(III) (TETA) is higher than that of Gd(DOTA), its kinetic and thermodynamic stabilities are lower. Accordingly, Gd(III) chelates based on 1,4,7-triazacyclodecane (DETA) are the compromise of neutrality, high water relaxivity and stability [Bucher, E., Cortes, S., Chavez, F., Sherry, A. D., 1991, Inorg. Chem., 30, 2092]. Introduction of a substitutent at one of the carbon on of a substitutent at one of the carbon atoms further enhances these properties.

One of the challenges on the preparation of azamacrocyles has been the cyclization reaction, since addition of the linker required for biomolecule derivatization to one of the reactants often decreases the yield of the desired macrocycle dramatically. Recently, the problem has been solved by performing the cyclization reaction between an appropriately substituted diol and a pernosylated amine under Mitsunobu conditions [Hovinen, J., Sillanpää, R. 2005, Tetrahedron Lett., 46, 4387].

In this reaction bulky substituents in the close proximity of the reaction centres facilitate the formation of the azamacrocycle.

An additional challenge on the preparation of azamacrocycles is their chemical nature. Since the unprotected azamacrocycles are basic, highly polar, nonchromophoric compounds, their purification and isolation is difficult.

SUMMARY OF THE INVENTION

The main object of the present invention is to provide derivatives of azacycloalkanes which allow biomolecule derivatization in solution and on solid phase. These derivatives can be used in diagnostic and therapeutic applications. Accordingly, they are suitable for in vitro diagnostics, molecular imaging, and they can be used as radiopharmaceuticals. When tethered to oligonucleotides, certain metal chelates based on azacrowns act as site specific cleavage agents of their target sequences. Accordingly, they can be utilized in chemotherapy as antisense oligonucleotides.

The major advantages of the present invention are:
(i) The present azamacrocycles have an aromatic ring in the linker arm, which is advantageous for their preparation, since the aromatic ring increases the yield of the cyclization reaction. The aromatic ring also serves as a chromophore which simplifies purification and isolation procedures.
(ii) The substitutent at the carbon atom (i.e. the aryloxy group) increases the kinetic and thermodynamic stabilities of the chelates.
(iii) The synthetic strategy is versatile enabling attachment of different linkers to the aromatic ring e.g. using Sonogashira reaction.
(iv) The azacrown derivatives are applicable for solid phase or solution phase labeling of bioactive molecules.

Thus, the present invention concerns a labeling reactant of a formula (I) suitable for labeling of bioactive molecules,

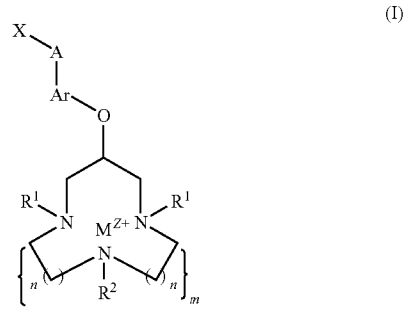

(I)

wherein
Ar is selected from the group consisting of phenyl, pyrenyl, anthracenyl and naphtyl;
A is a linker, formed from one to ten moieties, each moiety being selected from the group consisting of phenylene, alkyl containing 1-12 carbon atoms, ethenediyl (—C≡C—), ethenediyl (—C═C—); ether (—O—), thioether (—S—), amide (—CO—NH— and —NH—CO— and —CO—NR$^4$ and —NR$^4$—CO—), carbonyl (—CO—), ester (—COO— and —OOC—), disulfide (—SS—), diaza (—N═N—) or a tertiary amine (—NR$^4$—), where R$^4$ represents an alkyl containing less than 5 carbon atoms;
R$^1$ and R$^2$, same or different, are either protecting groups or a radical of acetic acid, acetate or acetate ion or a radical of

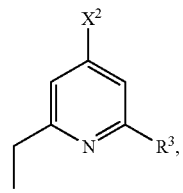

wherein R$^3$ is carboxylic acid, carboxylate ion, or an ester and X$^2$ is selected from the group consisting of furyl, trimethoxyphenyl and phenylethynyl, where the phenyl is substituted or unsubstituted or X$^2$ is not present;
X is a group for conjugation of the said labeling reactant to a biospecific binding reactant;
M is a metal or is not present;
the indexes n, which are same or different, are 1 or 2;
m is 1 or 2;
z is 2 or 3.

According to another aspect, the invention concerns a biospecific binding reactant (biomolecule) conjugated with the labeling reactant or a chelate derived from the labeling reactant according to this invention.

DETAILED DESCRIPTION OF THE INVENTION

Figure 1:
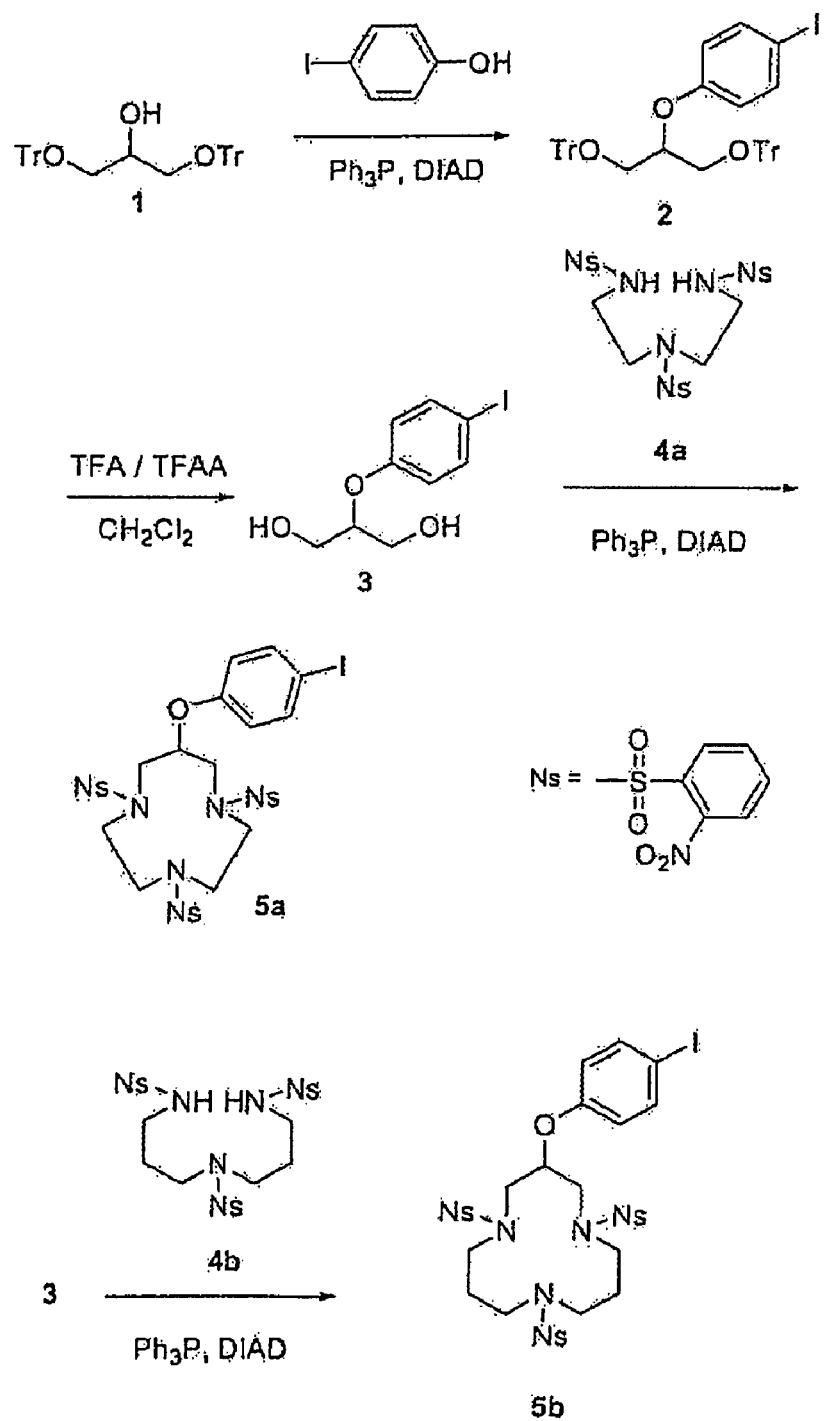
FIG. 1 illustrates exemplary synthetic routes to make compounds 3-(4-Iodophenoxy)-tris-(2-nitrobenzenesulfonyl)-1,4,7-triazacyclodecane, 5a, and 3-(4-Iodophenoxy)-tris-(2-nitrobenzenesulfonyl)-1,5,9-triazacyclodocecane, 5b.
Figure 2:
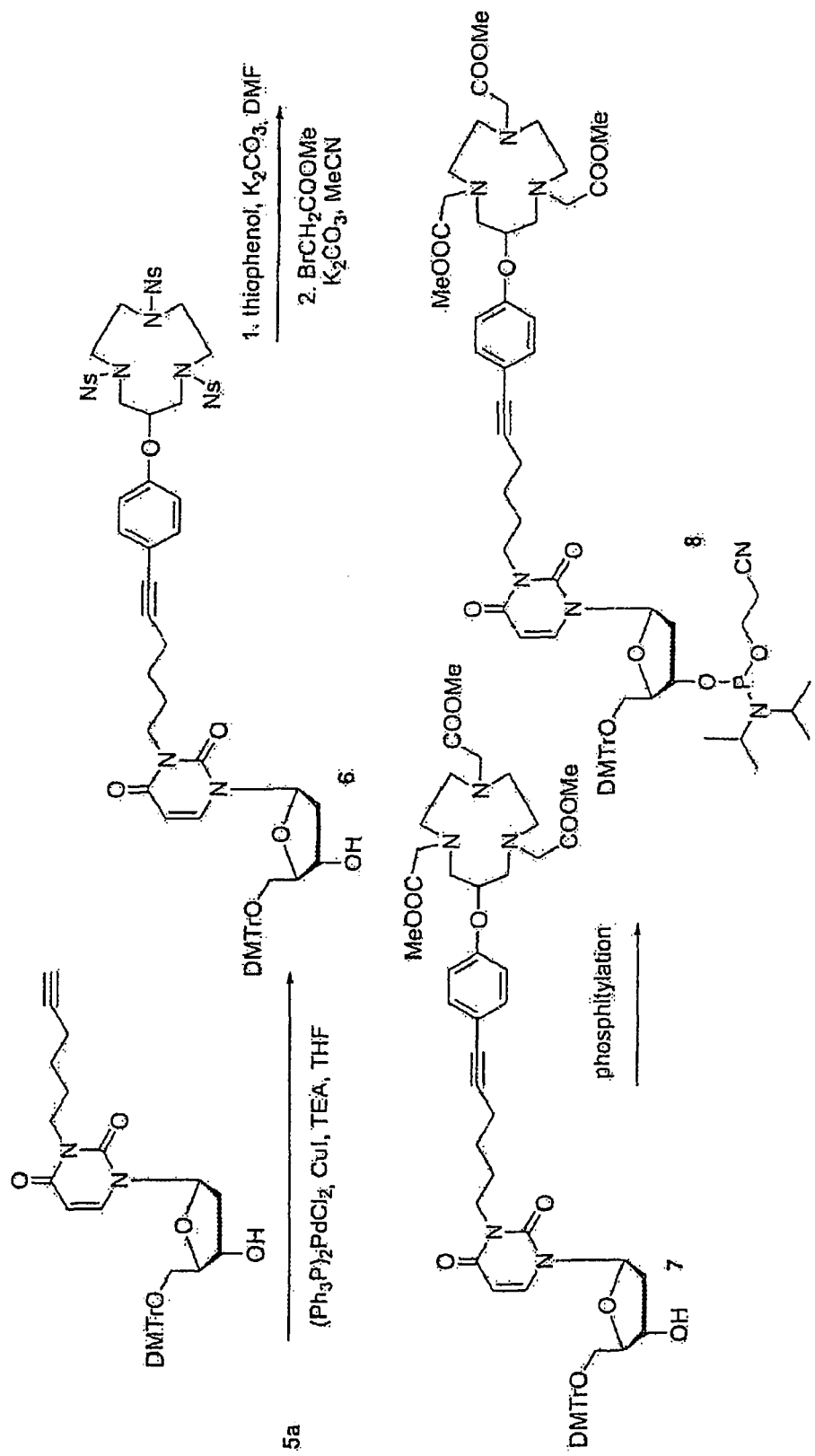
FIG. 2 illustrates an exemplary synthetic route to make compounds 2"-deoxy-5'-O-(4,4"-dimethoxytrityl)-3-[5-hexyn-1-yl-(4-phenoxy)tris-(2-nitrobenzenesulfonyl)-1,4,7-triazacyclodecanoyl]uridine, 6,2"-deoxy-5'-O-(4,4"-dimethoxytrityl)-3-[5-hexyn-1-yl-(4-phenoxy)tris-(methylacetato)-1,4,7-triazacyclodecanoyl]uridine, 7, and 2"-deoxy-5'-O-(4,4"-dimethoxytrityl)-3-[5-hexyn-1-yl-(4-phenoxy)tris-(methylacetato)-1,4,7-triazacyclodecanoyl] uridine 3'-O-(2-cyanoethyl-N,N-diisopropyl)phosphoramidite, 8.
Figure 3:
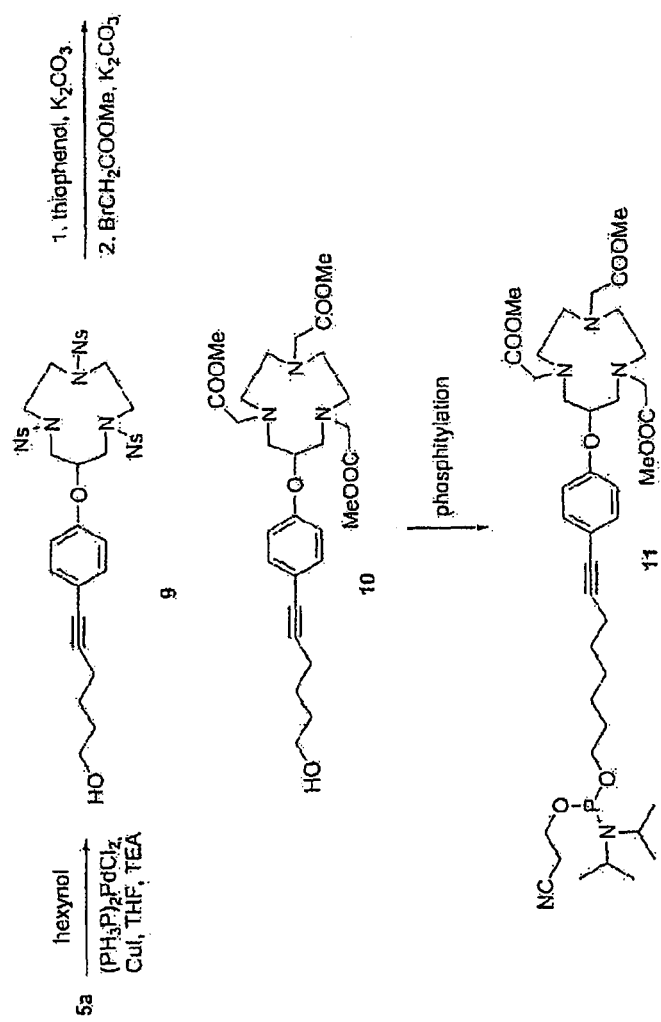
FIG. 3 illustrates an exemplary synthetic route to make compounds 5-hexyn-1-yl-(4-phenoxy)tris-(2-nitrobenzenesulfonyl)-1,4,7-triazacyclodecane, 9,5-hexyn-1-yl-(4-phenoxy)-1,4,7-(methoxycarbonylmethyl)-1,4,7-triazacyclodecane, 10, and 5-3-{4-{[(2-cyanoethyl-N,N-diisopropyl)phosphoramidito]-1-yl}phenoxyl]}1,4,7-tris (methoxycarbonylmethyl)-1,4,7-triazacyclodecane, 11.
Figure 4:
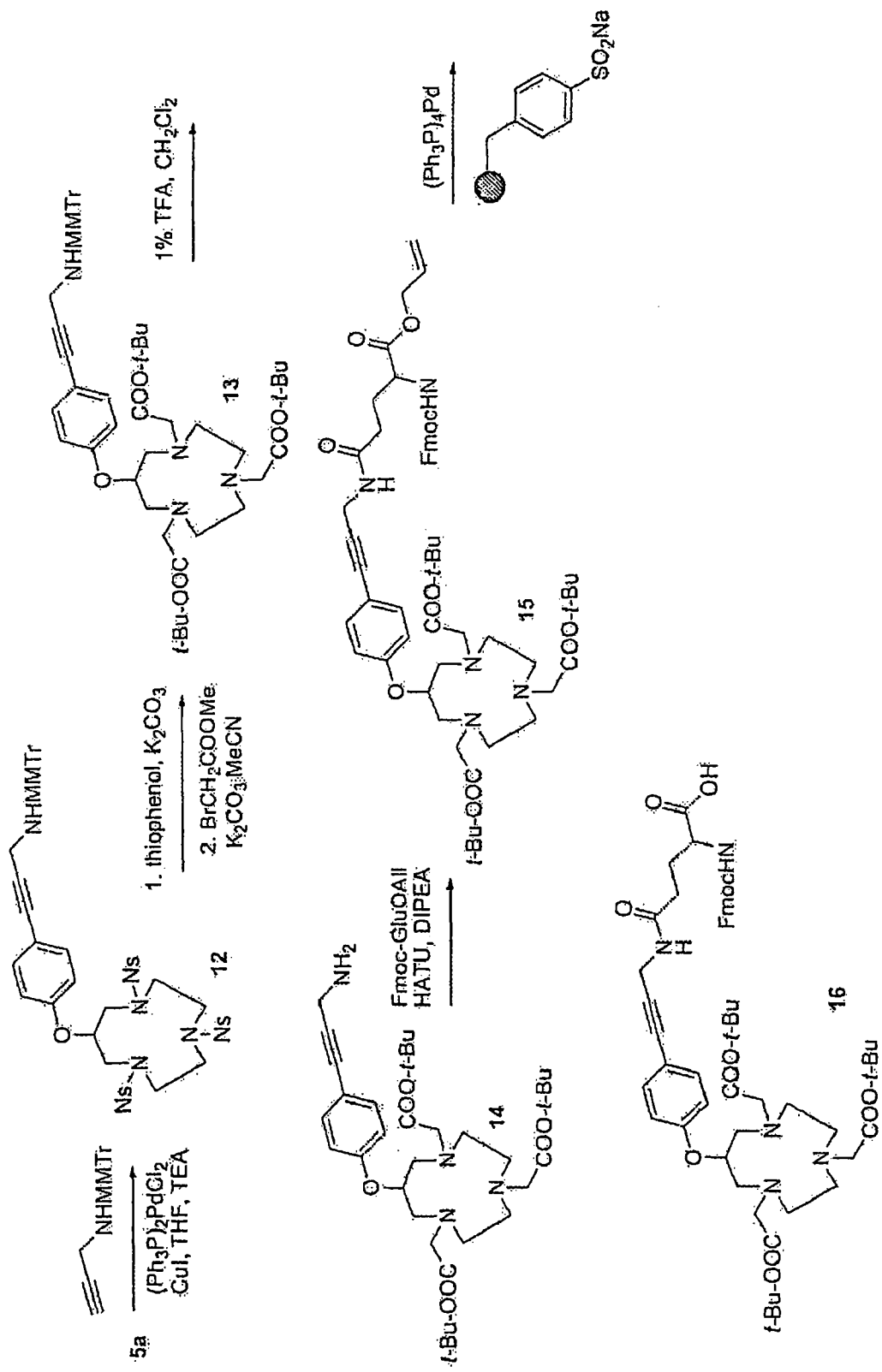
FIG. 4 illustrates an exemplary synthetic route to make compounds 3-(4-methoxytritylpropargylaminphenoxy)-tris-(2-nitrobenzenesulfonyl)-1,4,7-triazacyclodecane, 12, 3-(4-methoxytritylpropargylaminphenoxy)-1,4,7-tri-(t-butoxycarbonylmethyl)-1,4,7-triazacyclodecane, 13, 3-[4-propargylamino)phenoxy]-1,4,7-tri-(t-butyloxycarbonylmethyl)-1,4,7-triazacyclodecane, 14, 3-{4-{4'-{2-[4-allyloxycarbonyl-4-(fluorenylmethyloxycarbonylamino)] butyrylamidopropynyl}phenoxy}-1,4,7-tri-(t-butyloxycarbonylmethyl)-1,4,7-triazacyclodecane, 15, and 3-{4-{4'-{2-[4-carboxy-4-(fluorenylmethyloxycarbonylamino)]butyrylamidopropynyl}phenoxy}-1,4,7-tri-(t-butyloxycarbonylmethyl)-1,4,7-triazacyclodecane, 16.
Figure 5:
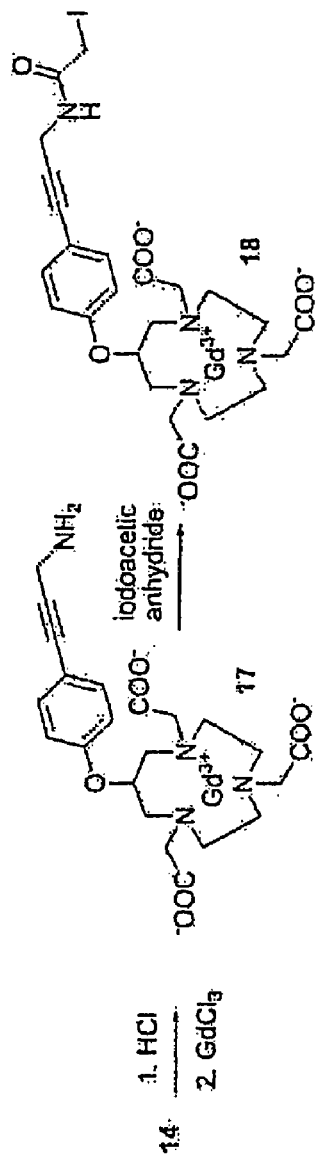
FIG. 5 illustrates an exemplary synthetic route to make compounds 3-(4-aminopropargyl)phenoxy-1,4,7-triazacyclodecane 1,4,7-triacetic acid gadolinium(III), 17, and 3-(4-iodoacetamidopropargyl)phenoxy-1,4,7-triazacyclodecane 1,4,7-triacetic acid gadolinium(III), 18.
Figure 6:
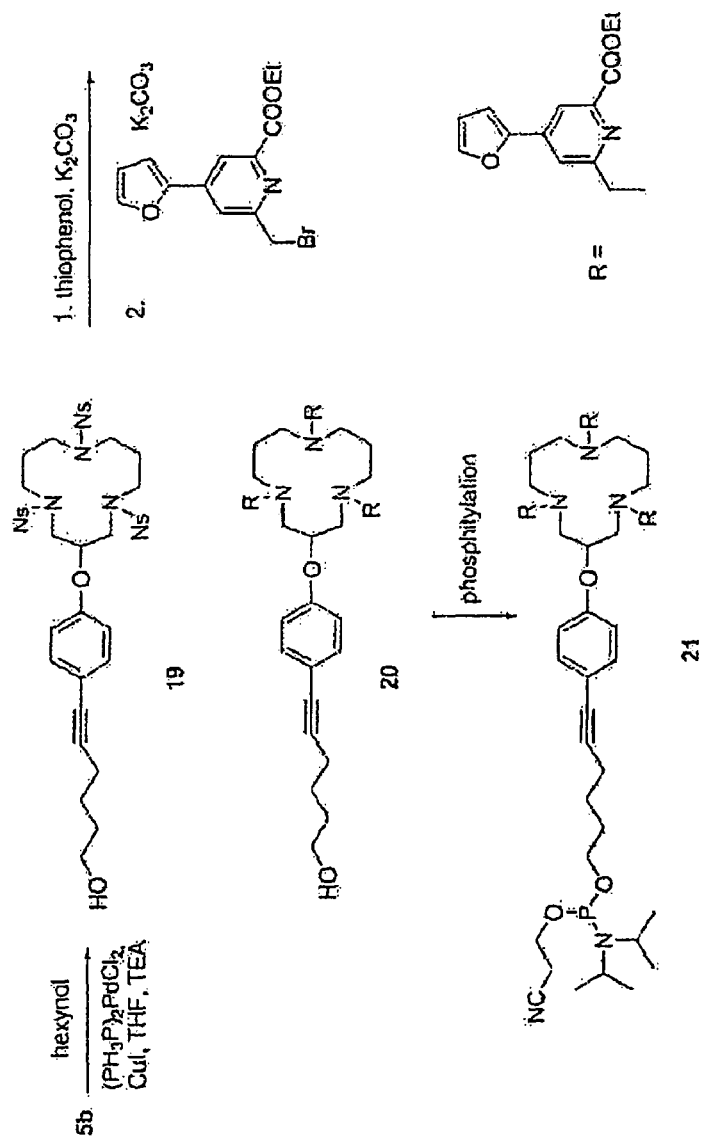
FIG. 6 illustrates an exemplary synthetic route to make compounds 3-(4-(6-hydroxyhexyn-1-yl)phenoxy)-tris-(2-nitrobenzenesulfonyl)-1,5,9-triazacyclododecane, 19, 3-(4-6-hydroxyhexyn-1-yl)phenoxy-1,5,9-tris[2-ethoxycarbonyl-4-(furan-2-yl)pyridin-2-ylmethyl]-1,5,9-triazacyclododecane, 20, and 1,5,9-tris[2-ethoxycarbonyl-4-(furan-2-yl)pyridin-2-ylmethyl]-3-{4-{[(2-cyanoethyl-N,N-diisopropyl)phosphoramidito]-1-yl}phenoxy]}-1,5,9-triazacyclododecane, 21.

According to a preferable embodiment, the aromatic ring is selected from phenyl, naphthyl, anthracenyl, or pyrenyl.

Preferably $R^1$ and $R^2$, same or different, are either protecting groups selected from trifluoroacetyl, nitrobenzenesulfonyl, t-butoxycarbonyl or fluorenylmethoxycarbonyl, or $R^1$ and $R^2$, same or different, are the acetic acid ester, wherein the ester is preferably ethyl, methyl, t-butyl or benzyl ester.

Where $R^3$ is an ester, the ester is most preferably ethyl, methyl or t-butyl ester.

Where $X^2$ is a chromophoric moiety it is preferably furyl, trimethoxyphenyl or ethynylphenyl, where the phenyl can be substituted or unsubstituted.

According to a preferable embodiment, the reactive group —X— is selected from amino, aminooxy, haloacetamido, the said halide being preferably bromide or iodide, isothiocyanato, 3,5-dichloro-2,4,6-triazinylamino, maleimido, carboxylic acid, an aldehyde, a thioester or an active ester of a carboxylic acid.

Where X is an active ester of a carboxylic acid, said ester is preferably an N-hydroxysuccinimido, p-nitrophenol or pentafluorophenol ester.

According to another preferable embodiment, X is formed from Z-E, where Z is a bridge point and is absent or is a radical of a purine base or a pyrimidine base or a 7-deazapurine base or any other modified base suitable for use in the synthesis of modified oligonucleotides, said base being connected to E via either i) a hydrocarbon chain, which is substituted with a protected hydroxyethyl or hydroxymethyl group, or via ii) a furan ring or pyrane ring or any modified furan or pyrane ring, suitable for use in the synthesis of modified oligonucleotides; and E is either a phosphorylating moiety

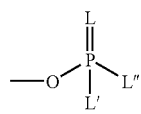

where L is absent or is O or S;
L' is H, L'''CH$_2$CH$_2$CN or L'''Ar', where Ar' is phenyl or its substituted derivative, where the substituent is nitro or chlorine, and L''' is O or S;
L'' is O$^-$, S$^-$, Cl, N(i-Pr)$_2$; or
E is a solid support tethered to Z via a linker arm, which is the same as or different from the linker -A- as defined above.

Preferably, the bridge point Z is a radical of any of the bases thymine, uracil, adenine, guanine or cytosine, deazaadenine or deazaguanine and said base is connected to E via either i)
a hydrocarbon chain, which is substituted with a protected hydroxyethyl or hydroxymethyl group, or via ii) a furan ring having a protected hydroxymethyl group in its 4-position and optionally a hydroxyl, protected hydroxyl, halogen, most preferably fluorine, or modified hydroxyl group in its 2-position.

According to another preferable embodiment, Z is a radical of adenine, cytosine or 7-deazaadenine where the exocyclic amino group is protected with a protecting group. The protecting group is preferably a benzoyl group. Other preferable protecting groups are, for example isobutyryl, dimethylformamidine, acetyl, t-butylphenoxyacetyl or phenoxyacetyl.

According to another preferable embodiment, Z is a radical of guanine or 7-deazaguanine where the exocyclic amino group is protected with a protecting group. The protecting group is preferably an isobutyryl group, but also other protecting groups can be used, for example dimethylformamidine, t-butylphenoxyacetyl or p-isopropylphenoxyacetyl.

Especially preferable are labeling reactants in which the furan ring in Z is derived from 2-deoxy-D-ribose.

Especially preferable are labeling reactants wherein E-Z-A is selected from the group consisting of the nine structures shown below:

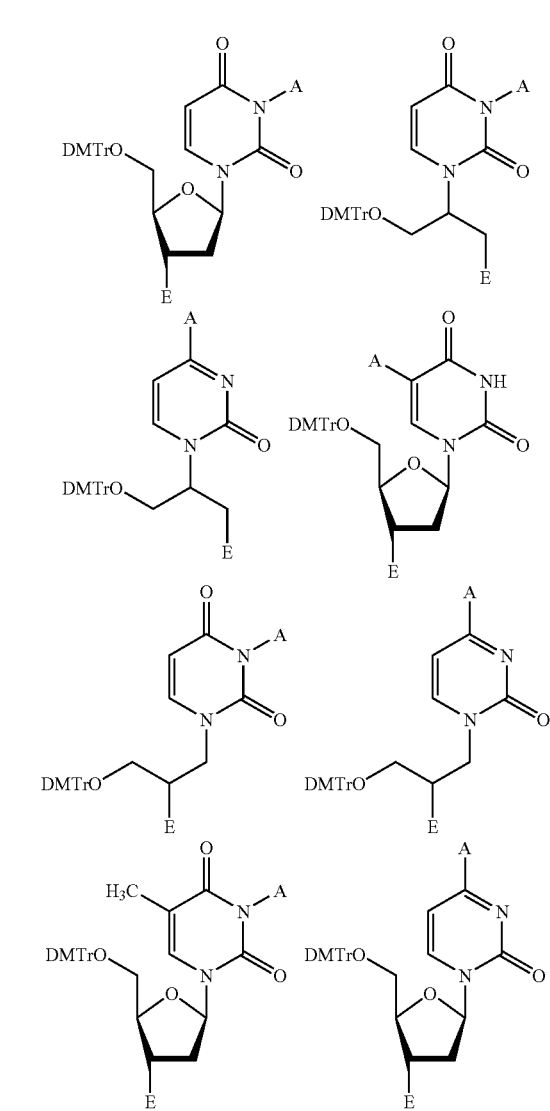

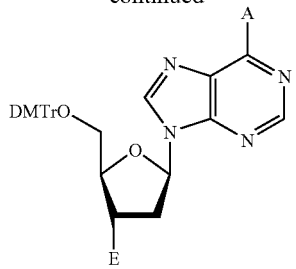

wherein DMTr is dimethoxytrityl.

According to a preferable embodiment, L is absent, L' is OCH₂CH₂CN and L" is N(i-Pr)₂.

The chelating agent can be introduced into oligonucleotides with the aid of oligonucleotide synthesizer. A useful method, based on a Mitsonobu alkylation (J Org Chem, 1999, 64, 5083; Nucleosides, Nucleotides, 1999, 18, 1339) is disclosed in U.S. Pat. No. 6,949,696 and U.S. Ser. No. 09/985,454 (AP100695). Said patent publications disclose a method for direct attachment of a desired number of conjugate groups to the oligonucleotide structure during chain assembly. Thus solution phase labeling and laborious purification procedures are avoided. The key reaction in the synthesis strategy towards nucleosidic oligonucleotide building blocks is the aforementioned Mitsunobu alkylation which allows introduction of various chelating agents to the nucleoside, and finally to the oligonucleotide structure. The chelating agents are introduced during the chain assembly. Conversion to the metal chelate takes place after the synthesis during the deprotection steps.

Normal, unmodified oligonucleotides have low stability under physiological conditions because of its degradation by enzymes present in the living cell. It may therefore be desirable to create a modified oligonucleotide according to known methods so as to enhance its stability against chemical and enzymatic degradation.

Modifications of oligonucleotides are extensively disclosed in prior art. Reference is made to U.S. Pat. No. 5,612,215. It is known that removal or replacement of the 2'-OH group from the ribose unit in an RNA chain gives a better stability. WO 92/07065 and U.S. Pat. No. 5,672,695 discloses the replacement of the ribose 2'-OH group with halo, amino, azido or sulfhydryl groups. U.S. Pat. No. 5,334,711 discloses the replacement of hydrogen in the 2'-OH group by alkyl or alkenyl, preferably methyl or allyl groups. Furthermore, the internucleotidic phosphodiester linkage can, for example, be modified so that one or more oxygen is replaced by sulfur, amino, alkyl or alkoxy groups. Preferable modification in the internucleotide linkages are phosphorothioate linkages. Also the base in the nucleotides can be modified.

According to another preferable embodiment, X is a group suitable for labeling of oligopeptides. Here X is formed from $X^3(NHZ^2)$—, where $Z^2$ is a transient protecting group and $X^3$ is a carboxylic acid or its salt, acid halide or active ester.

Where $X^3$ is an active ester of a carboxylic acid, said ester is preferably an N-hydroxysuccinimido, p-nitrophenol or pentafluorophenol ester. Where $X^3$ is an acid halide of a carboxylic acid, said halide is preferably chloride or fluoride.

The transient protecting group $Z^2$ is preferably fluorenylmethoxycarbonyl (Fmoc); nitrobenzenesulfonyl (Ns); tert-butoxycarbonyl (Boc) or 1,1-dioxobenzo[b]thio-phen-2-yl-methyloxycarbonyl (Bsmoc).

The labeling reactant according to the present invention is preferably one of the following:

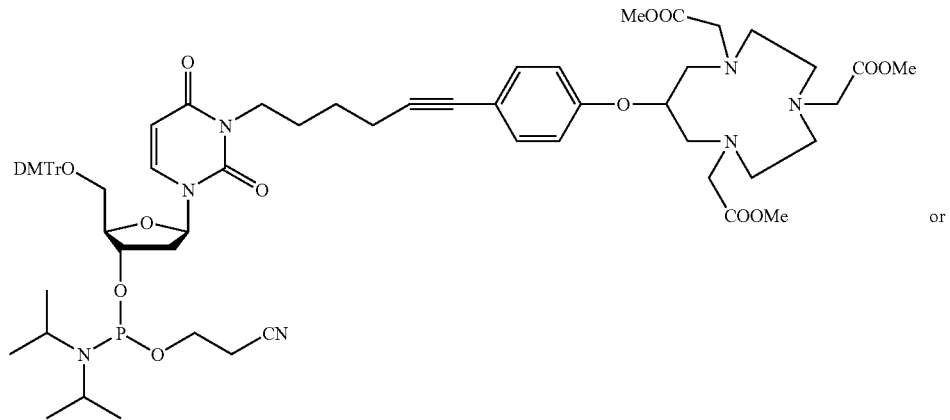

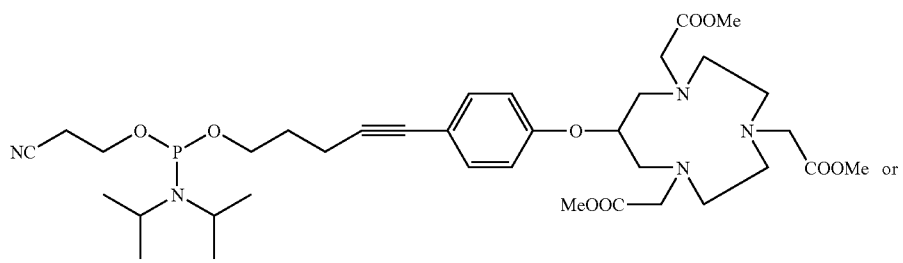

-continued
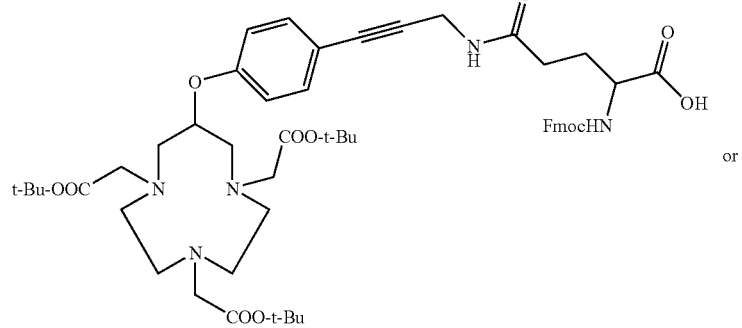
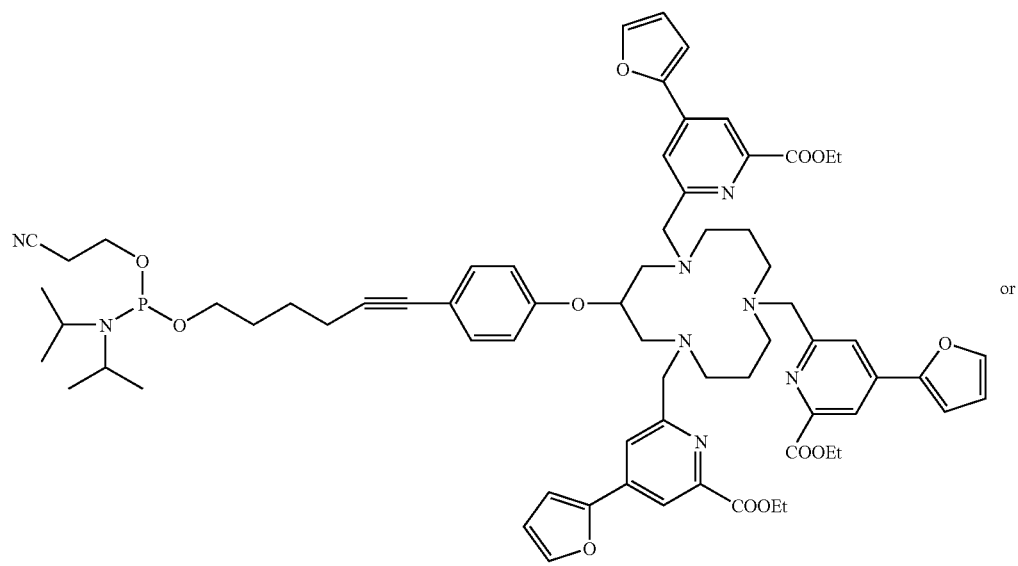
or
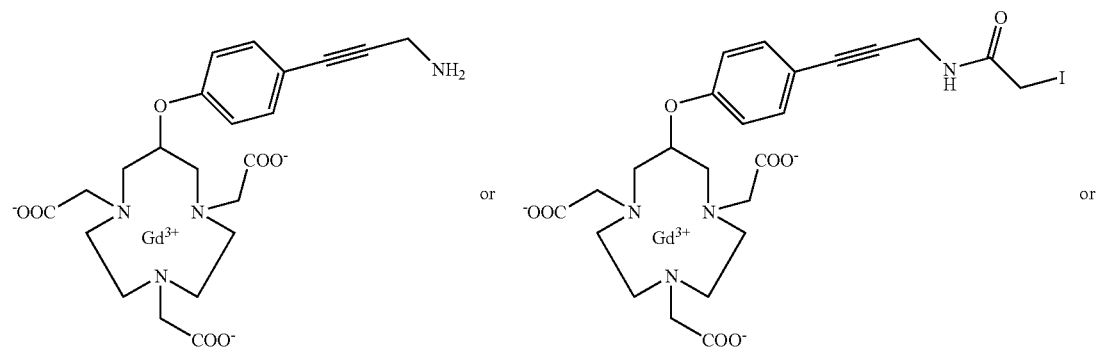
or

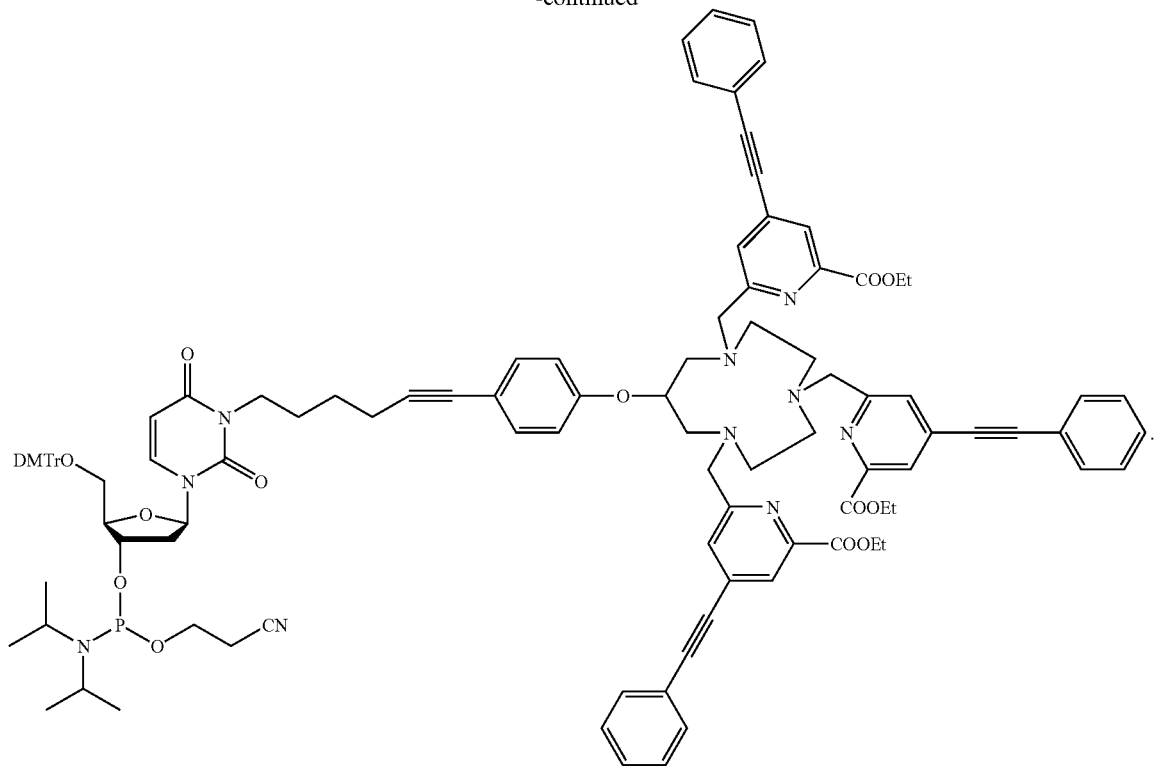

According to a preferable embodiment the metal M is a metal suitable for use in bioaffinity assays such as a lanthanide or a metal suitable for use in positron emission tomography (PET), single positron emission tomography (SPECT) or magnetic resonange imaging (MRI).

A preferable metal to be used in MRI is gadolinium. However, also lanthanides, particularly europium (III), but also other lanthanides such as samarium (III) and dysprosium (III) are useful in MRI applications. In PET and SPECT applications a radioactive metal isotope is introduced into the chelating agent just before use. Particularly suitable radioactive isotopes are Ga-66, Ga-67, Ga-68, Cr-51, In-111, Y-90, Ho-166, Sm-153, Lu-177, Er-169, Tb-161, Tc-98m, Dy-165, Ho-166, Ce-134, Nd-140, Eu-157, Er-165, Ho-161, Eu-147, Tm-167 and Co-57.

Suitable metals for use in bioaffinity assays are lanthanides, especially europium (III), samarium (III), terbium (III) or dysprosium (III).

A suitable metal for RNA cleavage is Zn(II).

The biospecific binding reactant to be labeled is, for example, an oligonucleotide, oligopeptide, protein, oligosaccharide, polysaccharide, phospholipid, PNA, LNA, antibody, hapten, drug, receptor binding ligand or lectin.

The invention will be illuminated by the following non-restrictive Experimental Section.

EXPERIMENTAL SECTION

Figure 7:
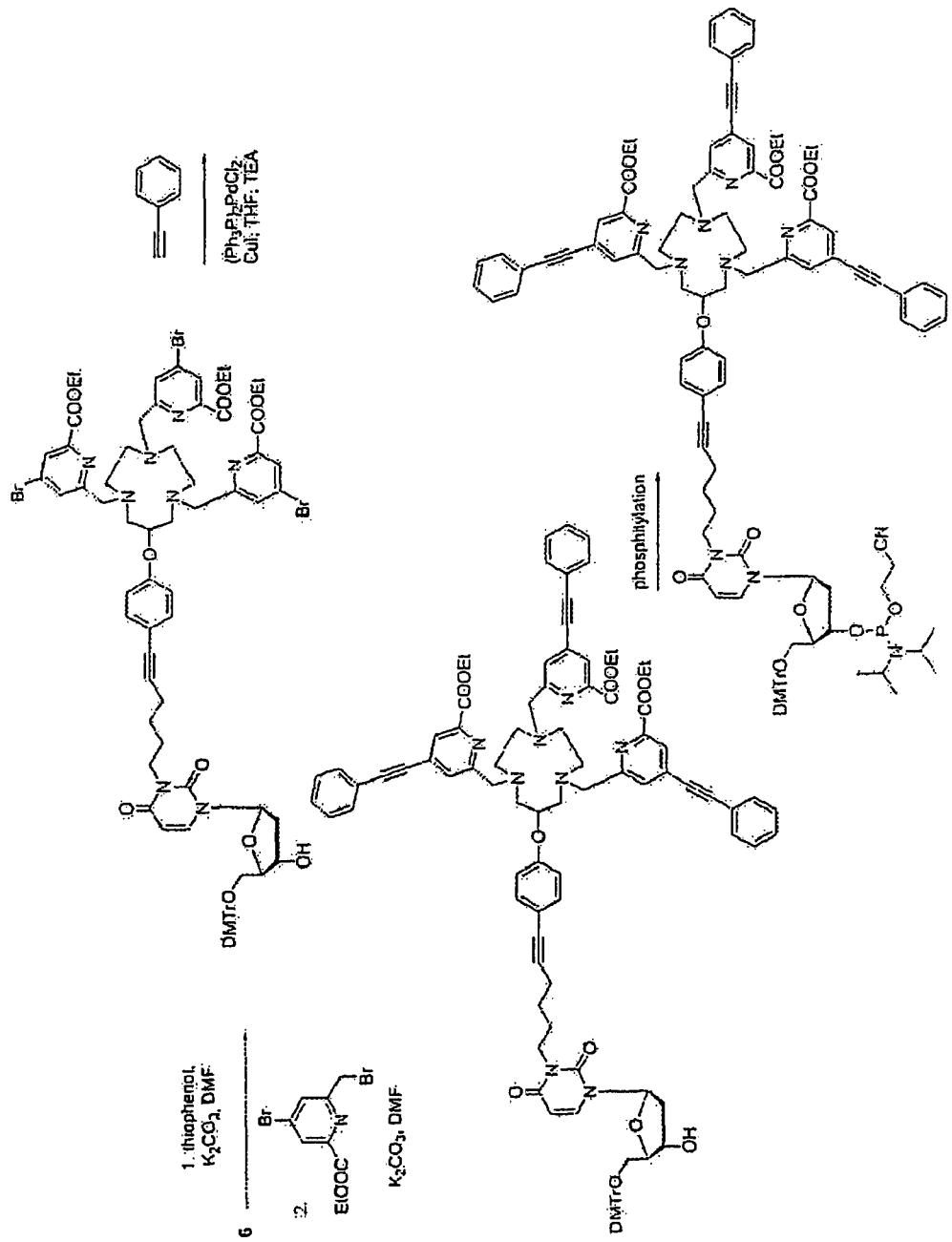
FIG. 7 illustrates a synthetic route for the preparation of an oligonucleotide labeling reactant designed for site-specific introduction of luminescent europium(III) chelates to oligonucleotides.

The invention is further elucidated by the following examples. The structures and synthetic routes employed in the experimental part are depicted in FIGS. 1-6. Experimental details are given in Examples 1-21. FIG. 7 illustrates the synthetic route for the preparation of an oligonucleotide labeling reactant designed to site-specific introduction of luminescent europium(III) chelates to oligonucleotides.

Procedures

Adsorption column chromatography was performed on columns packed with silica gel 60 (Merck). All dry solvents were from Merck and they were used as received. Sodium sulfinate resin (200-400 mesh, 1% DVB, 1.3 mmol $g^{-1}$) was purchased from Tianjin Nankai Hecheng Science & Technology Company Limited (China). NMR spectra were recorded on a Bruker 250 spectrometer operating at 250.13 MHz for $^1$H. The signal of TMS was used as an internal reference. ESI-TOF mass spectra were recorded on an Applied Biosystems Mariner instrument.

EXAMPLES

Example 1

The Synthesis of 1,3-bis(trityloxy)propan-2-ol, 1

Glycerol (5.0 g, 54.28 mmol) was dried by coevaporations with dry pyridine and dissolved in the same solvent (100 mL). Trityl chloride (45 g, 0.16 mol) was added portionwise, and the mixture was stirred overnight at RT. All volatiles were removed in vacuo. The residue was dissolved in dichloromethane, washed twice with sat $NaHCO_3$ and dried over $Na_2SO_4$. Precipitation from diethyl ether gave the title compound (30 g). $^1$H NMR ($CDCl_3$): 7.40-7.22 (30H) 3.94 (1H, m); 3.29 (4H, m); 2.29 (1H, d, J 5.9). ESI-TOF MS: required for $C_{41}H_{36}NaO_3$+599.26 (M+Na$^+$), found 599.21.

Example 2

The Synthesis of [2-(4-Iodophenoxy)-3-(trityloxy) propoxy]-triphenylmethane, 2

Compound 1 (5.0 g, 8.67 mmol), 4-iodophenol (2.10 g, 9.54 mmol) and triphenyl phosphine (2.5 g, 9.5 mmol) were dissolved in dry THF (35 mL). Diisopropyl azodicarboxylate (1.88 mL, 9.5 mmol) was added dropwise during 15 min, and the reaction was allowed to proceed overnight at RT. All volatiles were removed in vacuo. Purification on silica gel (eluent, petroleum ether, bp 40-60° C.: dichloromethane, 1:1, v/v) yielded 6.07 g of the title compound. $^1$H NMR (CDCl$_3$): 7.49 (2H, d, J 9.1); 7.37-7.21 (30H); 6.62 (2H, d, J 9.1). 4.43 (1H, m); 3.40 (4H, m).

Example 3

The Synthesis of
2-(4-Iodophenoxy)propane-1,3-diol, 3

Compound 2 (2.5 g, 3.21 mmol) was dissolved in dichloromethane (25 mL). A solution of trifluoroacetic acid and trifluoroacetic anhydride in dry dichloromethane (1.83 M; 50 mL) was added and the reaction was allowed to proceed for 15 min at RT. The mixture was cooled on ice-water bath, and it was made basic with triethylamine, poured into methanol and concentrated. Precipitation from the mixture of dichloromethane and petroleum ether gave the title compound. Yield was 86%. Mp. 90° C. $^1$H NMR (DMSO-d$_6$): 7.57 (2H, d, J 8.9); 6.83 (2H, d, J 8.9); 4.81 (2H, t, J 5.8); 4.22 (1H, m); 3.54 (4H, m).

Example 4

The Synthesis of 3-(4-Iodophenoxy)-tris-(2-nitrobenzenesulfonyl)-1,4,7-triazacyclodecane, 5a Compound 3 (1.00 g, 3.40 mmol), 1,4,7-(2-nitrobenzenesulfonyl)-diethylenetriamine (4a; 2.24 g, 3.40 mmol; prepared as disclosed in Kurosawa, W., Fukyyama, T., 2002, Org. Synth, 79, 186.) and triphenylphosphine (2.67 g, 10.2 mmol) were dissolved in dry THF (85 mL). Diisopropyl azodicarboxylate (2.00 mL, 10.2 mmol) was added in four portions during 15 min. The reaction was allowed to proceed overnight at RT and concentrated in vacuo. Purification on silica gel (eluent 1% v/v methanol in dichloromethane) followed by precipitation from diethyl ether yielded the title compound. $^1$H NMR (CDCl$_3$): 8.00 (1H, m); 7.87 (2H, dd, J 1.5 and 6.1), 7.79-7.58 (9H, m); 7.54 (2H, d, J 8.9); 6.88 (2H, d, J 8.9); 5.13 (1H, m); 4.10 (2H, dd, J 4.2 and 15); 3.82-3.62 (8H, m); 3.12 (2H, dd, J 4.5 and 15). ESI-TOF MS: required for C$_{31}$H$_{30}$IN$_6$O$_{13}$S$_3$$^+$ 917.01 (M+H)$^+$, found 916.96.

Example 5

The Synthesis of 3-(4-Iodophenoxy)-tris-(2-nitrobenzenesulfonyl)-1,5,9-triazacyclododecane, 5b The synthesis was performed as in Example 4 but using 1,5,9-(2-nitrobenzenesulfonyl)-dipropylenetriamine (4b; prepared as disclosed in Kurosawa, W., Fukyyama, T., 2002, Org. Synth, 79, 186). $^1$H NMR (CDCl$_3$): 7.95 (3H, m); 7.75 (2H, m); 7.66-7.60 (5H, m); 7.55 (2H, dd, J 1.5 and 7.7); 7.45 (2H, d, J 6.7); 6.49 (2H, d, J 6.7); 4.81 (1H, p, J 5.9); 3.77 (2H, dd, J 5.6 and 15); 3.73 (2H, m); 3.59-3.52 (4H, m); 3.36 (2H, m); 3.22 (2H, m); 2.28 (2H, m); 2.03 (2H, m). ESI-TOF MS: required for C$_{32}$H$_{34}$IN$_6$O$_{13}$S$_3$$^+$ 944.99 (M+H)$^+$, found 944.97.

Example 6

The Synthesis of 2'-deoxy-5'-O-(4,4'-dimethoxytrityl)-3-[5-hexyn-1-yl-(4-phenoxy)tris-(2-nitrobenzenesulfonyl)-1,4,7-triazacyclodecanoyl]uridine, 6

Compound 5a (0.50 g, 0.54 mmol) and 2'-deoxy-5'-O-(4,4'-dimethoxytrityl)-3-(5-hexyn-1-yl)uridine (0.37 g, 0.60 mmol; prepared as disclosed in Peuralahti, J., Jaakkola, L., Mukkala, V.-M., Hovinen, J., 2006, Bioconjugate Chem. In press) were dissolved in the mixture of dry THF (8 mL) and TEA (4 mL) and the mixture was deaerated with argon. (Ph$_3$P)$_2$PdCl$_2$ and CuI were added, and the mixture was stirred overnight at RT in dark, before being concentrated in vacuo. The residue was dissolved in dichloromethane, washed with water and dried over Na$_2$SO$_4$. Purification on silica gel (eluent 10% MeOH, v/v in dichloromethane) yielded the title compound. $^1$H NMR (CDCl$_3$): 7.89 (1H, m); 7.79 (2H, m); 7.67-7.47 (12H, m); 7.33-7.7.18 (12H, m); 6.88 (2H, d, J 8.5); 6.78 (4H, d, J 8.5); 6.22 (1H, t, J 6.1); 5.37 (1H, t, J 7.9); 5.03 (1H, m); 4.46 (1H, m); 4.01 (1H, m); 3.93 (2H, m); 3.68-3.55 (10H, m); 3.71 (6H, s); 3.36 (2H, m); 3.08 (2H, m); 2.34 (2H, t, J 6.7); 2.31 (1H, m); 2.17 (1H, m); 1.73 (2H, m); 1.54 (2H, m).

Example 7

The synthesis of 2-deoxy-5'-O-(4,4'-dimethoxytrityl)-3-[5-hexyn-1-yl-(4-phenoxy)tris-(methylacetato)-1,4,7-triazacyclodecanoyl]uridine, 7

Compound 6 (0.24 g, 0.17 mmol) was dissolved in dry DMF (5 mL). Thiophenol (60 μL) an potassium carbonate (0.2 g) were added, and the mixture was stirred overnight at RT before being filtered and washed with DMF. All volatiles were removed in vacuo. The residue was redissolved in DMF (3 mL). K$_2$CO$_3$ (0.2 g) and methyl bromoacetate (65 μL, 0.68 mmol) were added, and the mixture was heated overnight at 55° C. before being cooled to RT and filtered. The filtrate was concentrated, dissolved in dichloromethane, washed with sat. NaHCO$_3$ and dried over Na$_2$SO$_4$. Purification on silica gel (eluent 15% methanol in dichloromethane) yielded the title compound. $^1$H NMR (CDCl$_3$): 7.74 (1H, d, J 8.2); 7.39 (2H, d, J 6.7); 7.30 (9H, m); 6.84 (4H, d, J 8.7); 6.75 (2H, d, J 8.5); 6.33 (1H, t, J 6.4); 5.55 (1H, d, J 7.9); 4.55 (1H, m); 4.03 (1H, m); 3.96 (2H, m); 3.79 (9H, s); 3.71 (6H, s); 3.67 (6H, s); 3.45 (4H, m); 3.25-2.81 (tot. 12H); 2.42 (2H, m); 2.40 (1H, m); 2.25 (1H, m); 1.80 (2H, m); 1.66 (2H, m).

Example 8

The Synthesis of 2'-deoxy-5'-O-(4,4'-dimethoxytrityl)-3-[5-hexyn-1-yl-(4-phenoxy)tris-(methylacetato)-1,4,7-triazacyclodecanoyl]uridine 3-O-(2-cyanoethyl-N,N-diisopropyl)phosphoramidite, 8

Compound 7 was phosphitylated using the method disclosed in Hovinen, J., Hakala, H., 2001, Org. Lett., 3, 2473. $^{31}$P NMR (CDCl$_3$): 149.8 (0.5 P); 149.3 (0.5 P).

Example 9

The Synthesis of 5-hexyn-1-yl-(4-phenoxy)tris-(2-nitrobenzenesulfonyl)-1,4,7-triazacyclodecane, 9

Compound 5a was allowed to react with 5-hexynol using the method described in Example 6. $^1$H NMR (CDCl$_3$): 7.99 (1H, m); 7.87 (2H, m); 7.78-7.57 (9H, m); 7.29 (2H, d, J 8.8); 6.97 (2H, d, J 8.8); 5.12 (1H, m); 4.08 (2H, dd, J 4.6 and 14.8); 3.81-3.63 (10H, m); 3.13 (2H, dd, J 5.1 and 15.4); 2.42 (2H, t, J 6.6); 1.78-1.63 (4H, m); 1.32 (1H, t, J 4.7). ESI-TOF MS: required for C$_{37}$H$_{39}$N$_6$O$_{14}$S$_3$$^+$ 887.16 (M+H)$^+$, found 887.12.

Example 10

The Synthesis of 5-hexyn-1-yl-(4-phenoxy)-1,4,7-(methoxycarbonylmethyl)-1,4,7-triazacyclodecane, 10

Compound 9 was deprotected and converted to the corresponding methyl ester as described in Example 7. ESI-TOF MS: required for $C_{27}H_{40}N_3O_8^+$ 534.28 (M+H)$^+$, found 534.30.

Example 11

The Synthesis of 5-3-{4-{[(2-cyanoethyl-N,N-diisopropyl)phosphoramidito]-1-yl}phenoxy]}1,4,7-tris(methoxycarbonylmethyl)-1,4,7-triazacyclodecane, 11

Compound 10 was converted to the corresponding phosphoramidite as disclosed in Hovinen, J., Hakala, H., 2001, Org. Lett., 3, 2473. ESI-TOF MS: required for $C_{35}H_{54}N_5O_9P^+$ 719.37 (M+H)$^+$, found 719.34.

Example 12

The Synthesis of 3-(4-methoxytritylpropargylaminphenoxy)-tris-(2-nitrobenzenesulfonyl)-1,4,7-triazacyclodecane, 12

Compound 5a (0.17 g, 0.19 mmol) was coupled with (4-methoxytrityl)propargylamine as described in Example 5. Purification on aluminum oxide using dichloromethane as the eluent yielded the title compound. $^1$H NMR (CDCl$_3$): 7.99 (1H, m); 7.87 (2H, m); 7.79-7.55 (tot. 9H); 7.50 (3H, m); 7.40 (2H, d, J 8.9); 7.32-7.26 (5H, m); 7.20 (2H, m); 6.97 (2H, d, J 8.9); 6.88 (2H, d, J 8.9); 6.82 (2H, d, J 8.9); 5.12 (1H, m); 4.09 (2H, m); 3.81-3.61 (8H, m); 3.78 (3H, s); 3.14 (2H, s); 3.13 (2H, m). ESI-TOF MS: required for $C_{54}H_{49}N_7O_{14}S_3^+$ 1116.20 (M+H)$^+$, found 1116.24.

Example 13

The Synthesis of 3-(4-methoxytritylpropargylaminphenoxy)-1,4,7-tri-(t-butoxycarbonylmethyl)-1,4,7-triazacyclodecane, 13

Compound 12 was deprotected using the method described in Example 7. The resulting amine was redissolved in dry DMF. t-Butyl bromoacetate and potassium carbonate were added, and the mixture was heated overnight at 55° C. Work up and purification was performed as described in Example 7.

Example 14

The synthesis of 3-[4-propargylamino)phenoxy]-1,4,7-tri-(t-butyltoxycarbonylmethyl)-1,4,7-triazacyclodecane, 14

Compound 13 was dissolved in dichloromethane containing 1% (v/v) of TFA and stirred for 15 min at RT before being concentrated in vacuo. ESI-TOF MS: required for $C_{40}H_{49}N_8O_{13}S_3^+$ (M+triethylamine)$^+$ 945.26; found 945.30.

Example 15

The synthesis of 3-{4-{4-{2-[4-allyloxycarbonyl-4-(fluorenylmethyloxycarbonylamino)]butyrylamidopropynyl}phenoxy}-1,4,7-tri-(t-butyltoxycarbonylmethyl)-1,4,7-triazacyclodecane, 15

Fmoc-Glu-OAll (0.20 g, 0.50 mmol), HATU (0.30 g, 0.33 mmol) and DIPEA (0.15 mL, 0.80 mmol) were dissolved in dry DMF (2 mL), and the mixture was stirred for 20 min at RT. Compound 14 (0.30 mmol) was added and the mixture was stirred for an additional 2 h. The mixture was diluted with dichloromethane (50 mL), washed twice with 10% citric acid and dried over Na$_2$SO$_4$. Purification on silica gel (eluent CH$_2$Cl$_2$/MeOH 9:1, v/v) gave compound 15. ESI-TOF MS: required for $C_{57}H_{76}N_5O_{12}$(M+H)$^+$ 1022.55; found 1022.59.

Example 16

The Synthesis of 3-{4-{4'-{2-[4-carboxy-4-(fluorenylmethyloxycarbonylamino)]butyrylamidopropynyl}phenoxy}-1,4,7-tri-(t-butyltoxycarbonylmethyl)-1,4,7-triazacyclodecane, 16

Deprotection of compound 15 using the method disclosed in Peuralahti, J., Jaakkola, L., Mukkala, V.-M., Hovinen, J., 2006, Bioconjugate Chem. in press yielded compound 16. ESI-TOF MS: required for $C_{53}H_{69}N_5O_{12}$(M+H)$^+$ 967.49; found 967.52.

Example 17

The synthesis of 3-(4-aminopropargyl)phenoxy-1,4,7-triazacyclodecane 1,4,7-triacetic acid gadolinium (III) 17

Compound 14 was dissolved in conc. HCl and stirred for 3 h at RT before being concentrated in vacuo. The residue was dissolved in water, and pH was adjusted to 6 with solid NaHCO$_3$. Gadolinium(III) chloride hexahydrate (1.5 eq) was added, and the mixture was stirred overnight at RT (pH 6.5). pH was then rised to 10 with aq. NaOH, and gadolinium hydroxide precipitated was removed by centrifugation. The product was isolated by addition of acetone. ESI-TOF MS: required for $C_{22}H_{28}$ GdN$_4$O$_7$ (M+H)$^+$ 618.12; found 618.21.

Example 18

The Synthesis of 3-(4-iodoacetamidopropargyl)phenoxy-1,4,7-triazacyclodecane 1,4,7-triacetic acid gadolinium(III) 18

Compound 17 was converted to the corresponding iodoacetamido derivative using the method disclosed in Takalo et al, Bioconjugate Chem., 1994, 5, 278. ESI-TOF MS: required for $C_{24}H_{29}$ GdIN$_4$O$_8$ (M+H)$^+$ 786.03; found 786.05.

Example 19

The Synthesis of 3-(4-(6-hydroxyhexan-1-yl)phenoxy)-tris-(2-nitrobenzenesulfonyl)-1,5,9-triazacyclododecane, 19

Compound 5b (250 mg, 0.26 mmol) and 5-hexyn-1-ol (43 μL, 0.39 mmol) were dissolved in the mixture of dry THF (6 mL) and triethylamine (2 mL) and the mixture was deaerated with argon. Pd(Ph$_3$P)$_2$Cl$_2$ (3.6 mg, 0.005 mmol) and CuI (1.9 mg, 0.01 mmol) were added, and the mixture was stirred overnight at RT in dark. All volatiles were removed in vacuo. The residue was suspended in dichlormethane, washed twice with water and dried over $Na_2SO_4$. Purification on silica gel (eluent: MeOH: $CH_2Cl_2$, 1:9, v/v) yielded the title compound. $^1$H NMR ($CDCl_3$): 7.99 (1H, m); 7.87 (2H, m); 7.78-7.57 (tot 9H); 7.29 (2H, d, J 8.8); 6.97 (2H, d, J 8.8); 5.12 (1H, m); 4.08 (2H, dd, J 4.6 and 15); 3.81-3.69 (tot 10H); 3.13 (2H, dd, J 5.1 and 15); 2.42 (2H, t, J 6.6); 1.78-1.63 (tot 4H); 1.32 (1H, t, J 4.7). ESI-TOF MS: required for $C_{39}H_{43}N_6O_{14}S_3^+$ (M+H)$^+$ 915.19; found 915.24.

Example 20

The Synthesis of 3-(4-6-hydroxyhexan-1-yl)phenoxy-1,5,9-tris[2-ethoxycarbonyl-4-(furan-2-yl)pyridin-2-ylmethyl]-1,5,9-triazacyclododecane, 20

Compound 19 (0.50 g, 0.52 mmol) was deprotected using the method described in Example 7. The resulting amine was redissolved in DMF. 2-bromomethyl-6-ethoxycarbonyl-4-(furan-2-yl)pyridine (0.63 g, 2.04 mmol), synthesized as disclosed in U.S. patent application Ser. No. 10/928,143 and potassium carbonate were added, and the mixture was stirred overnight at 60° C. All insoluble material was removed by filtration, and the filtrate was concentrated in vacuo. Purification on aluminum oxide (eluent: MeOH: $CH_2Cl_2$, 1:9, v/v) yielded the title compound. $^1$H NMR ($CDCl_3$): 8.16 (3H, m); 7.93 (3H, m); 7.57 (2H, m); 7.26 (2H, d, overlapping with the signal of $CHCl_3$); 6.90 (3H, m); 6.79 (2H, d, J 3.4); 6.52 (2H, m); 6.46 (1H, m); 4.94 (1H, m); 4.47 (6H, q, J 7.1); 3.95 (2H, s); 3.84 (4H, s); 3.74 (2H, t, J 6.1); 3.42 (2H, m); 3.12 (2H, m); 2.95 (2H, m); 2.47 (2H, t, J 6.8); 1.74 (8H, m); 1.43 (9H, t, J 7.1). ESI-TOF MS: required for $C_{60}H_{67}N_6O_{11}^+$ (M+H)$^+$ 1047.49; found 1047.46.

Example 21

The Synthesis of 1,5,9-tris[2-ethoxycarbonyl-4-(furan-2-yl)pyridin-2-ylmethyl]-3-{4-{[(2-cyanoethyl-N,N-diisopropyl)phosphoramidito]-1-yl}phenoxy]}-1,5,9-triazacyclododecane, 21

Compound 20 was phosphitylated using the method disclosed in Hovinen, J., Hakala, H., 2001, Org. Lett., 3, 2473. ESI-TOF MS: required for $C_{69}H_{84}N_8O_{12}P^+$ 1247.59 (M+H)$^+$, found 1247.62.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A labeling reactant of formula (I)

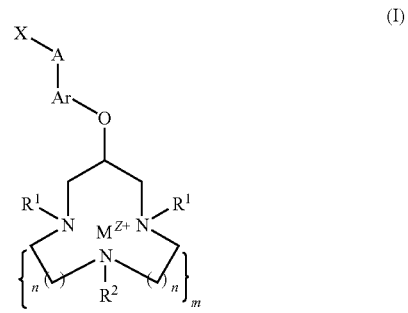

wherein

Ar is selected from the group consisting of phenyl, pyrenyl, antracenyl and naphtyl;

A is a linker, formed from one to ten moieties, each moiety being selected from the group consisting of phenylene, alkyl containing 1-12 carbon atoms, ethynediyl (—C≡C—), ethylenediyl (—C=C—); ether (—O—), thioether (—S—), amide (—CO—NH— and —NH—CO— and —CO—NR$^4$ and —NR$^4$—CO—), carbonyl (—CO—), ester (—COO— and —OOC—), disulfide (—SS—), diaza (—N=N—) or a tertiary amine (—NR$^4$—), where R$^4$ represents an alkyl containing less than 5 carbon atoms;

R$^1$ and R$^2$, same or different, are either protecting groups selected from among trifluoroacetyl, nitrobenzenesulfonyl, t-butoxycarbonyl and fluorenylmethoxycarbonyl, or R$^1$ and R$^2$, same or different, are an acetic acid ester or a radical of

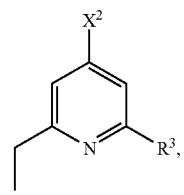

wherein R$^3$ is carboxylic acid, carboxylate ion, or an ester and X$^2$ is selected from the group consisting of furyl, trismethoxyphenyl and phenylethynyl, where the phenyl is substituted or unsubstituted or X$^2$ is not present;

X is a group for conjugation of the said labeling reactant to a biospecific binding reactant;

wherein the reactive group X is selected from amino, aminooxy, haloacetamido, isothiocyanato, 3,5-dichloro-2,4,6-triazinylamino, maleimido, a thioester or an active ester of a carboxylic acid, or the reactive group X is formed from Z-E, where Z is absent or is a radical of a purine base or a pyrimidine base or a 7-deazapurine base, said bases being connected to E via either i) a hydrocarbon chain, which is substituted with a protected hydroxyethyl or hydroxymethyl group, or via ii) a furan ring or pyrane ring; and E is either a phosphorylating moiety

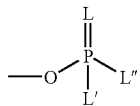

where
L is absent or is O or S;
L" is H, L'''CH$_2$CH$_2$CN or L'''Ar', where Ar' is phenyl or its substituted derivative, where the substituent is nitro or chlorine, and L''' is O or S; L" is O⁻, S⁻, Cl, N(i-Pr)$_2$; or
E is a solid support tethered to Z via a linker arm, which is the same as or different from the linker -A- as defined above;

or the reactive group X is formed from X$^3$(NHZ$^2$)—, where Z$^2$ is a transient protecting group and X$^3$ is a carboxylic acid or its salt, acid halide or active ester;
M is a metal or is not present;
the indexes n, which are same or different, are 1 or 2;
m is 1 or 2;
z is 2 or 3.

2. The labeling reactant according to claim 1 wherein the metal is a lanthanide.

3. The labeling reactant according to claim 1 where the metal is selected from the group consisting of gallium-67, gallium-68, technetium-98m, europium, terbium, samarium, gadolinium and dysprosium.

4. The labeling reactant according to claim 1 where the labeling reactant is

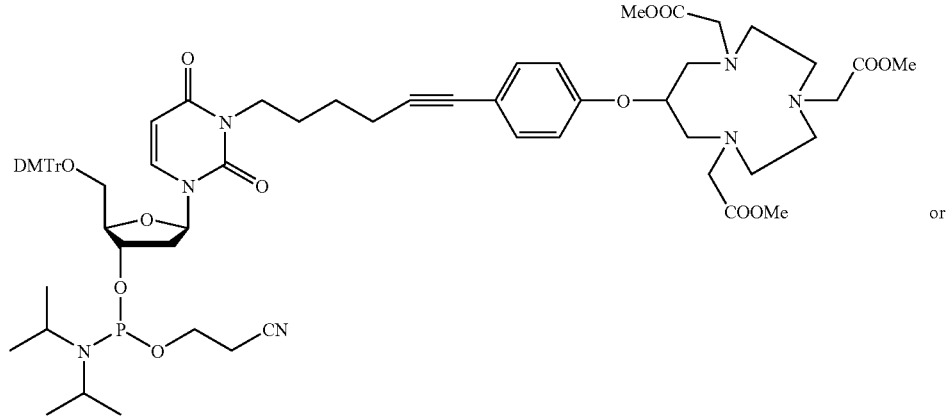

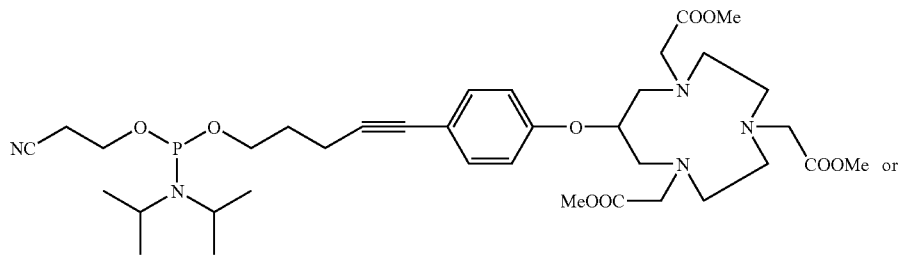

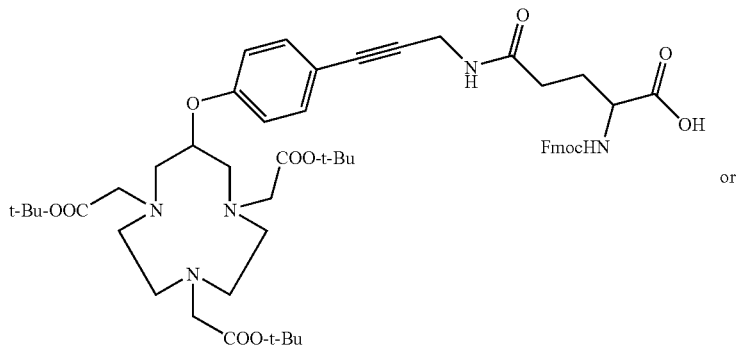

-continued
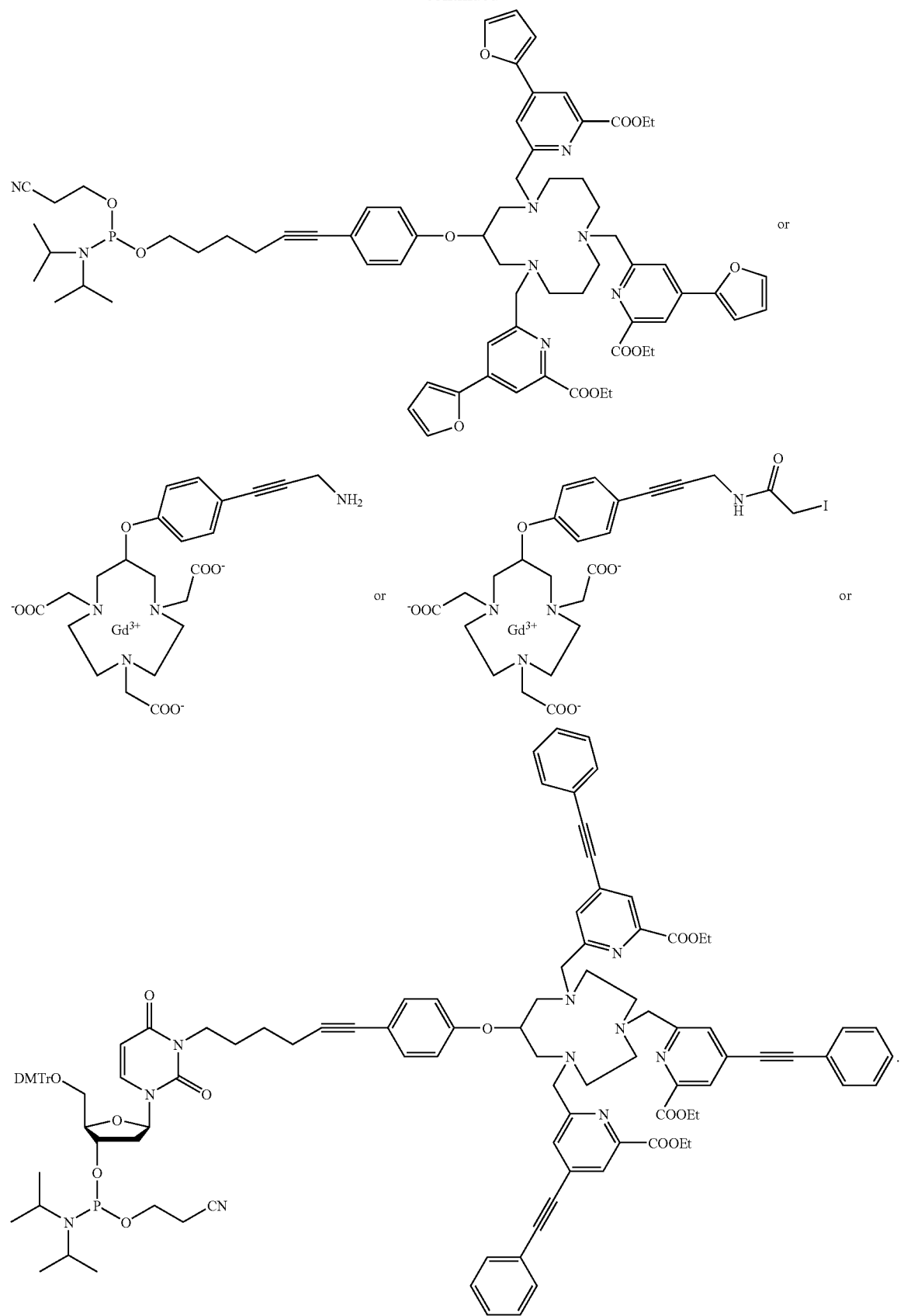

5. A conjugate comprising a biospecific binding reactant conjugated with a labeling reactant according to claim 1, wherein the biospecific binding reactant is an oligopeptide, protein, deoxyribonucleic acid, ribonucleic acid, oligosaccaride, polysaccaride, phospholipide, PNA, LNA, antibody, hapten, drug, receptor binding ligand or lectine.

6. The labeling reactant according to claim 1, wherein the reactive group X is bromoacetamido or iodoacetamido.

7. The labeling reactant according to claim 1, wherein the reactive group X is a thioester or an active ester of a carboxylic acid, said ester being a N-hydroxysuccinimido, p-nitrophenol, or pentafluorophenol ester.

8. The labeling reactant according to claim 1, wherein said acetic acid ester is selected from among ethyl, methyl, t-butyl and benzyl ester.

\* \* \* \* \*